(12) United States Patent
Adkins et al.

(10) Patent No.: US 8,635,901 B2
(45) Date of Patent: Jan. 28, 2014

(54) FOLDED PASSAGE GAS CHROMATOGRAPHY COLUMN

(75) Inventors: Douglas R. Adkins, Albuquerque, NM (US); Patrick Lewis, Albuquerque, NM (US)

(73) Assignee: Defiant Technologies, Inc., Albuquerque, MN (US)

( * ) Notice: Subject to any disclaimer, the term of this patent is extended or adjusted under 35 U.S.C. 154(b) by 512 days.

(21) Appl. No.: 12/916,483

(22) Filed: Oct. 29, 2010

(65) Prior Publication Data
US 2011/0226040 A1    Sep. 22, 2011

Related U.S. Application Data

(60) Provisional application No. 61/340,409, filed on Mar. 17, 2010.

(51) Int. Cl.
*G01N 30/60* (2006.01)
(52) U.S. Cl.
USPC ............................ 73/23.39; 73/23.35

(58) Field of Classification Search
USPC ............................................. 73/23.35, 23.39
See application file for complete search history.

(56) References Cited

U.S. PATENT DOCUMENTS

| | | | | |
|---|---|---|---|---|
| 4,935,040 | A * | 6/1990 | Goedert | 73/23.22 |
| 6,660,069 | B2 * | 12/2003 | Sato et al. | 96/4 |
| 2005/0223775 | A1 * | 10/2005 | Klee et al. | 73/23.41 |
| 2006/0283324 | A1 * | 12/2006 | Roques | 96/101 |

* cited by examiner

*Primary Examiner* — Hezron E Williams
*Assistant Examiner* — Paul West
(74) *Attorney, Agent, or Firm* — Gerald Grafe

(57) ABSTRACT

Embodiments of the present invention provide columns for use in gas chromatography and methods of making and using such columns. The present invention provides a folded passage column: a fluid passage formed by joining a first channel in a first surface through a slot to a second channel in a second surface. In some embodiments, a folded passage column repeats that building block, joining a plurality of channels in a first surface with a plurality of channels in a second surface such that the channels link to form a continuous passage.

30 Claims, 11 Drawing Sheets

FOLDED PASSAGE GAS CHROMATOGRAPHY COLUMN

CROSSREFERENCE TO RELATED APPLICATIONS

This application claims priority to U.S. provisional application 61/340,409, filed Mar. 17, 2010, which is incorporated herein by reference.

BACKGROUND

The present invention relates to columns for use in gas chromatography and methods of making and using such columns.

Gas chromatography is a standard technique for separating compounds in gas samples for composition analysis. Typically, a gas sample is injected into a fused silica capillary column, and constituents of the sample separate based on each constituent compound's affinity for a coating on the interior wall of the capillary. Some compounds move rapidly through the column exhibiting little interaction with the column's coating, while other compounds move slowly through the column because of strong interactions with the coating.

Gas chromatography columns are typically 1 to 30 meters long, and have an inner diameter of 50 to 520 microns. Creating a compact gas chromatography (GC) column is challenging because it is difficult to bend fused silica capillaries to a radius much smaller than 100 mm. In the late 1990's, techniques were developed to etch spiral channels in silicon and cover the channel with a lid to produce rectangular cross-section columns (Overton, U.S. Pat. No. 6,068,684). Heaters or coolers are attached to these columns to provide controlled temperature profiles that aid in sample separations (Manginell, et al, U.S. Pat. No. 6,666,907 and Robinson, et al, U.S. Pat. No. 6,706,091).

Techniques have been developed to produce circular cross section columns in nickel from stacked sheets with an array of holes (U.S. Pat. No. 7,273,517). In this process, nickel is deposited on a plastic mold to form a thin sheet with an array of holes. Multiple sheets are stacked together to form an array of columns. Through the same deposition process, sheets with an array of slots are formed in nickel, and the slotted-sheets are stacked on the sheets with holes in such a way to form a continuous, serpentine passage. The entire stack is diffusion bonded together to create a single-chip GC column. With GC columns formed in this process, a 1-meter long column can be packaged in a chip that is approximately 13-mm on each side 1-mm thick. Longer columns have been formed by adding layers of hole-patterned sheets to the stack.

A drawback to the nickel micro-GC column is that multiple sheets with an array of holes are used in forming the stack. The thickness of the sheet is dictated by the time allocated to the deposition process; typically, each layer will be only 200 microns thick, so 5 layers would be required to make a 1 meter column. Each of these sheets must be accurately aligned in the stack to insure a uniform column, and each of the layers must be lapped flat and parallel to insure that the seal formed in diffusion bonding is hermetic. Also, the cross-section is not perfectly circular in the slotted passages that link holes in the array. Ideally, the cross-section would be uniform throughout the column to achieve the best chromatography. In a 30×30 array of these holes, there are 900 such slotted inter-linking passages that will perturb the flow profile through the nickel micro-GC column. Reducing the number of flow perturbations is important to improve chromatography.

There is a need for improved columns for use in gas chromatography.

SUMMARY OF THE INVENTION

Embodiments of the present invention provide columns for use in gas chromatography and methods of making and using such columns.

The advantages and features of novelty that characterize the present invention are pointed out with particularity in the claims annexed hereto and forming a part hereof. However, for a thorough understanding of the invention and the methods of its making and using, reference should be made to the drawings which form a further part hereof, and to the accompanying descriptive matter in which there are illustrated and described example embodiments of the present invention. The description below involves specific examples; those skilled in the art will appreciate other examples from the teachings herein, and combinations of the teachings of the examples.

BRIEF DESCRIPTION OF THE DRAWINGS

The accompanying drawings, which are incorporated in and form part of the specification, illustrate the present invention and, together with the description, describe the invention by way of various example embodiments.

DESCRIPTION OF THE INVENTION

As used herein, a "folded passage column" means any fluid passage formed by joining a first channel in a first surface through a slot to a second channel in a second surface. A "folded passage column" often repeats that building block, joining a plurality of channels in a first surface with a plurality of channels in a second surface such that the channels link to form a continuous passage.

Figure 1:
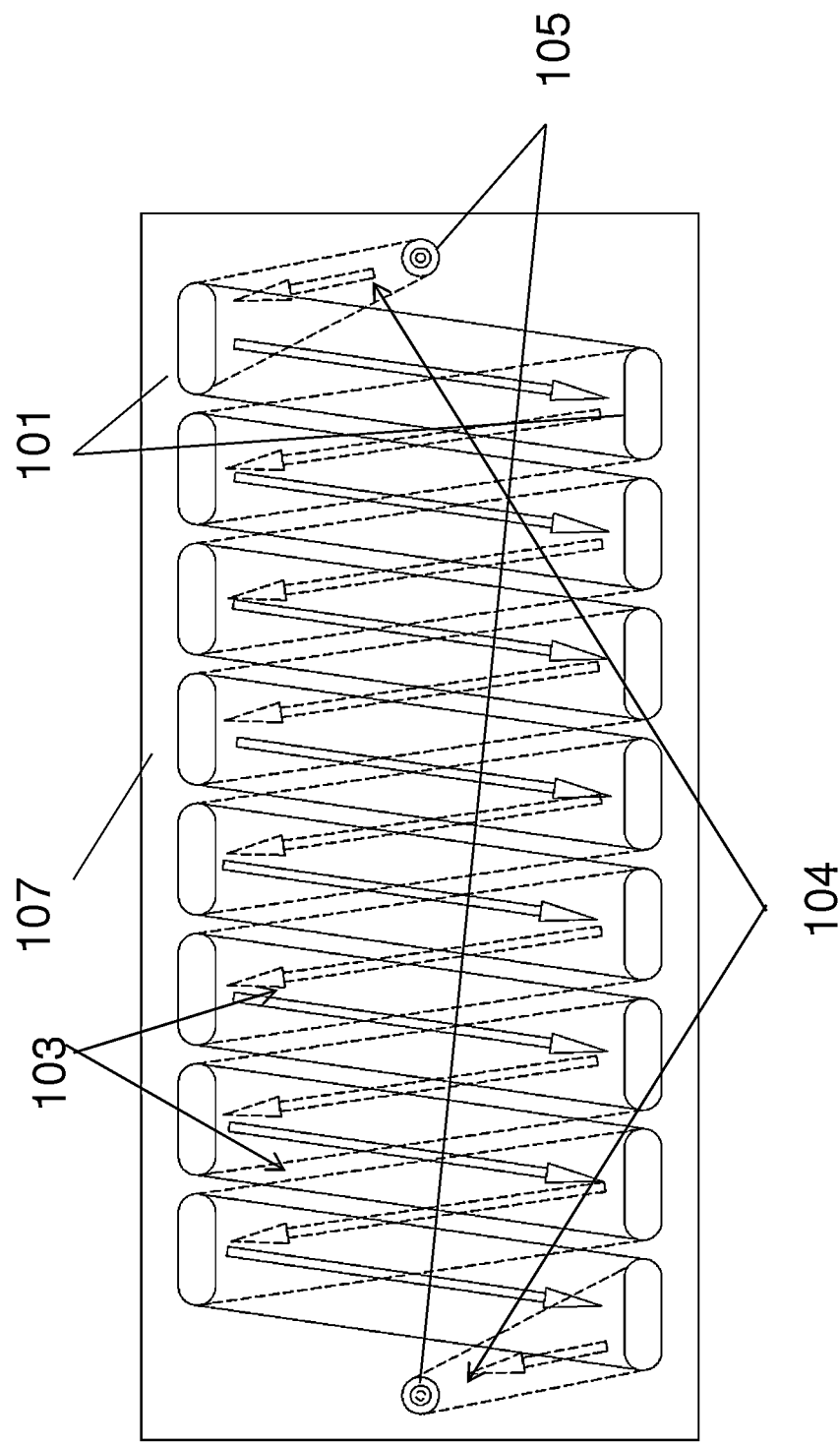
FIG. 1 is a schematic illustration of an example embodiment of the present invention.
Figure 2:
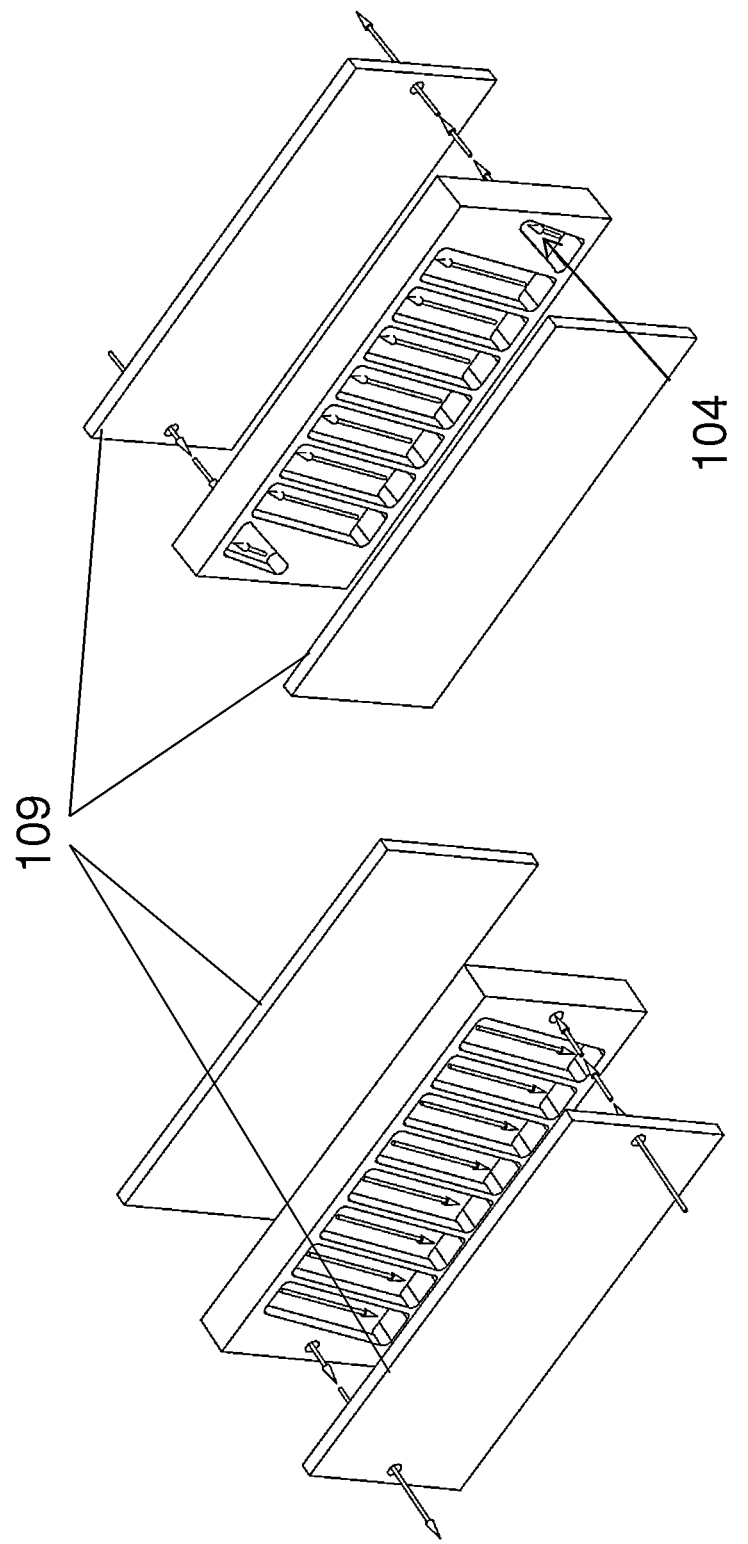
FIG. 2 is a schematic illustration of an example embodiment of the present invention.

FIG. 1 is a schematic illustration of an example apparatus according to the present invention. In FIG. 1, slots 101 form fluid connections between channels 103 in the surface of a plate 107. FIG. 2 comprises exploded views of an example apparatus as in FIG. 1 with caps 109. The left image is a port side view; the right image is the capped side of the column. Arrows indicate the flow path through the column in both figures. Channels 103, 104 are formed in each of the two opposing surfaces of the plate 107. The channels 103 are formed such that their ends can be communicated via slots 101, with each channel 103 communicating with two channels 107 on the opposing surface of the plate 107, except for channels 104 which communicate with a port 105 of the column. Channels 103, 104 together form a column, with which fluids can be communicated (introduced and withdrawn) via ports 105.

Figure 3:
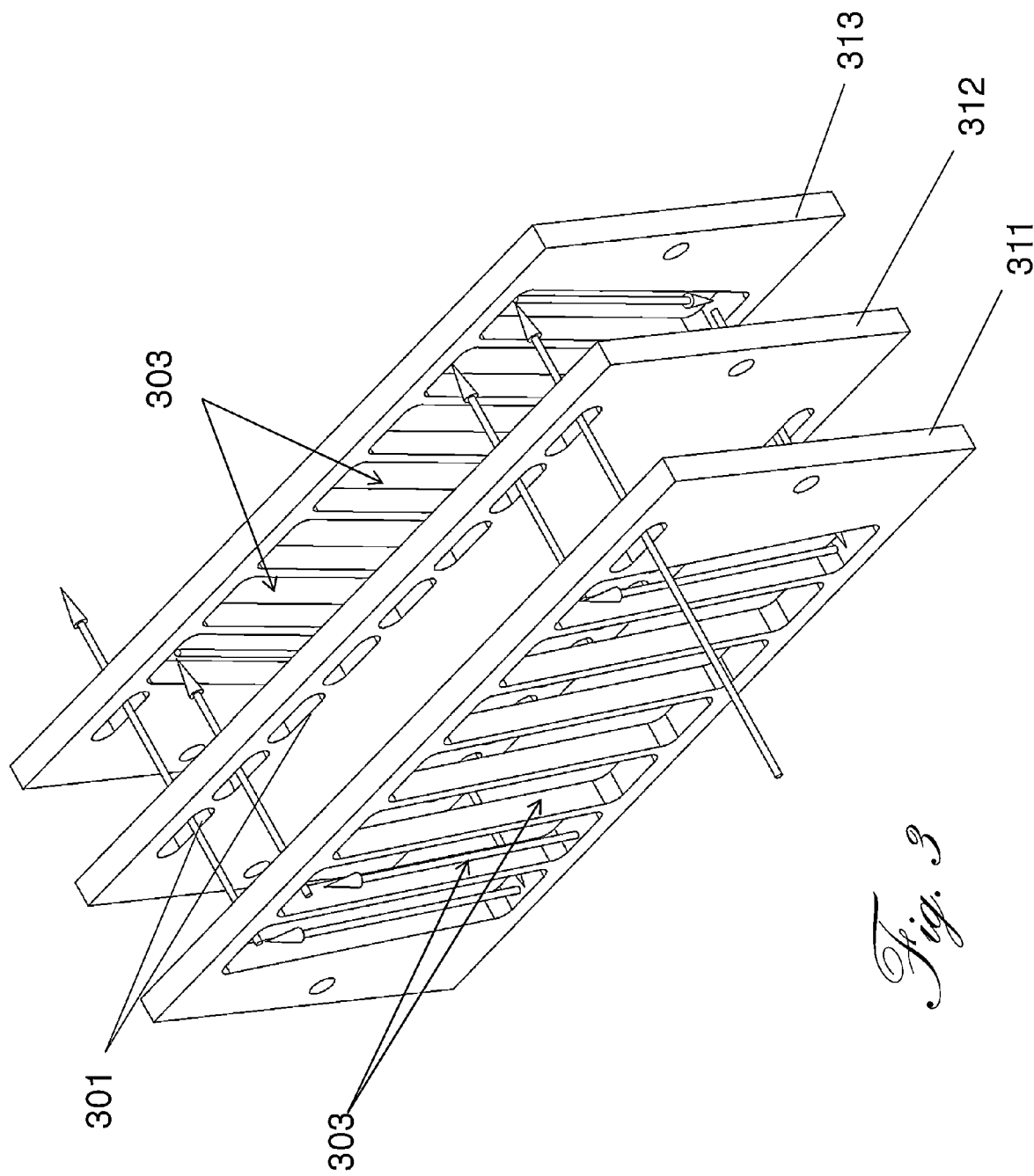
FIG. 3 is a schematic illustration of an example embodiment of the present invention.

FIG. 3 is a schematic illustration of an example apparatus according to the present invention. The example embodiment comprises first 311 and second 313 channel plates, and a slot plate 312. Channels 303 are formed as complete perforations of the channel plates 311, 313. Slots 301 that allow the channels 303 to communicate are formed as perforations through the slot plate 312. Channels 303 are disposed in the channel plates 311, 313 such that each channel communicates via slots 301 with two other channels 303, with the channels 303 all together forming a long column. Cover plates (not shown in FIG. 3) can be mounted with the outer surfaces of channel plates 311, 313 in a manner similar to that illustrated in FIG. 2.

Figure 4:
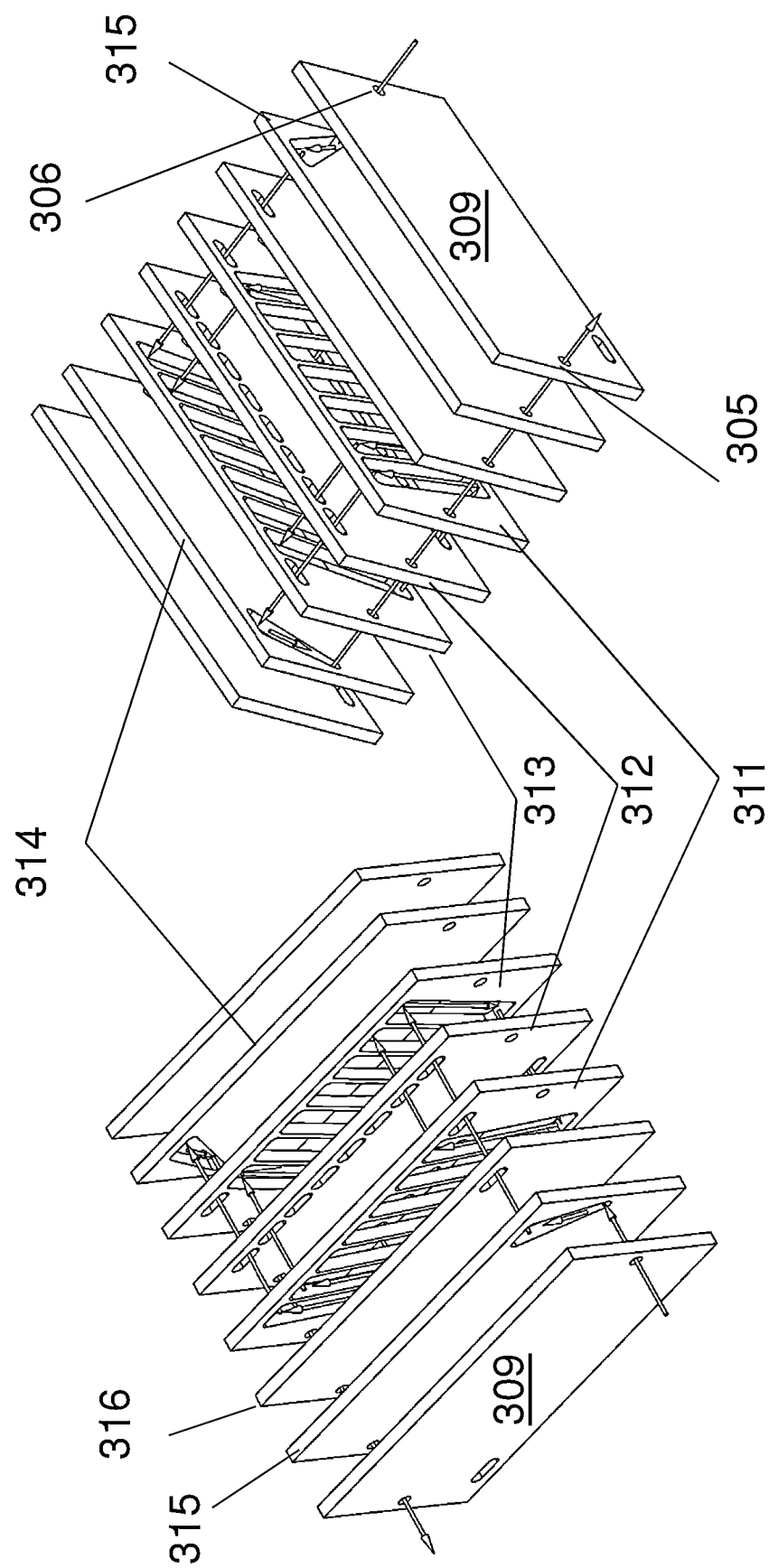
FIG. 4 is a schematic illustration of an example embodiment of the present invention.

FIG. 4 is a schematic illustration of an example embodiment of the present invention. The example embodiment comprises channel plates 311, 313 and slot plate 312 as described in connection with FIG. 3. A first transition plate 314 mounts with channel plate 313, sealing the channels therein and providing for communication with a port 305 formed by through holes in the channel plates 311, 313 and slot plate 312, allowing port 305 to exit from the side of the completed stack of plates distal from the first transition plate 314. A second transition plate 315 communicates with the other end of the completed column and with a second port 306. An intermediate transition plate 316 can be used to communicate between channel plate 311 and transition plate 315, allowing the transition plates 314, 315 to have the same design. Plate 316 also serves as a cover on the channels in plate 311 to form an enclosed passage. Plate 316 prevents gas that enters plate 309 from proceeding to the hole in plate 311 and thereby exiting the column before passing through the entire passage. First and second cover plates 309 seal the stack and provide for communication with the column via ports 305, 306.

Figure 5:
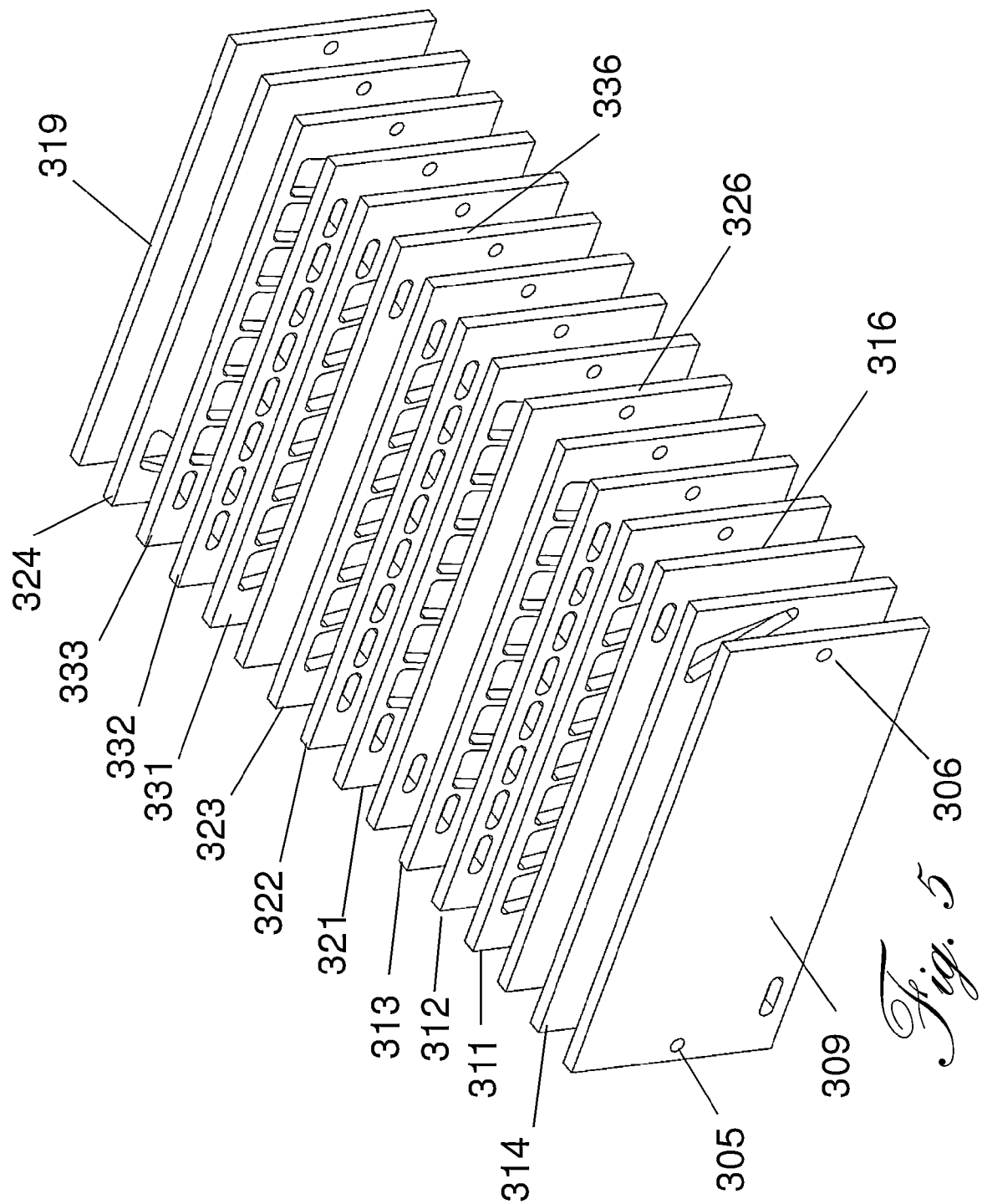
FIG. 5 is a schematic illustration of an example embodiment of the present invention.

FIG. 5 is a schematic illustration of an example embodiment of the present invention. Channels in channel plate 311 communicate with channels in channel plate 313 via slot plate 312 in a manner similar to that discussed in connection with preceding figures. The example embodiment comprises two additional similar trios of plates (321, 322, 323, and 331, 332, 333). The first set (311, 312, 313) communicates via a slot in an intermediate plate 326 with the second set (321, 322, 323), which in turn communicates via a slot in an intermediate plate 336 with the third set (331, 332, 333). Transition plates 314, 314 allow the channel-based column to communicate with ports 305, 306. Plate 316 prevents port 306 from communicating with corresponding ports in the proceeding plates. Plate 316 also provides a slot for fluid entering 306 to proceed to 311 and the remaining channel plates. Plates 316 and 319 can be identical. Cover plates 309, 319 mount with the stack and provide for communication with the column via ports 305, 306. With appropriate sizing and angles of the channels and slots, only a few unique plate designs are needed (channel, slot, auxiliary slot, e.g.) to form long columns.

Figure 6:
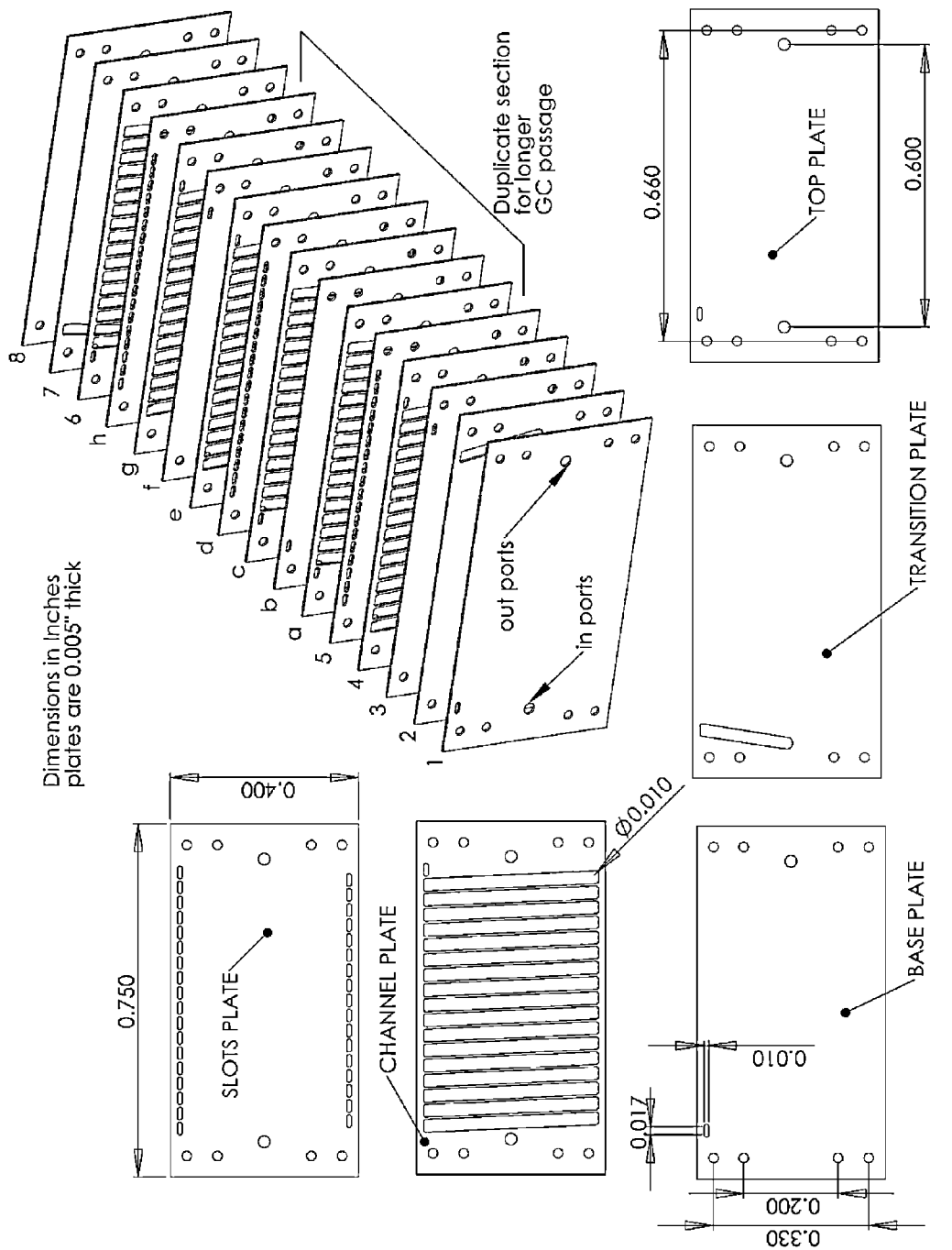
FIG. 6 is a schematic illustration of an example embodiment of the present invention.
Figure 7:
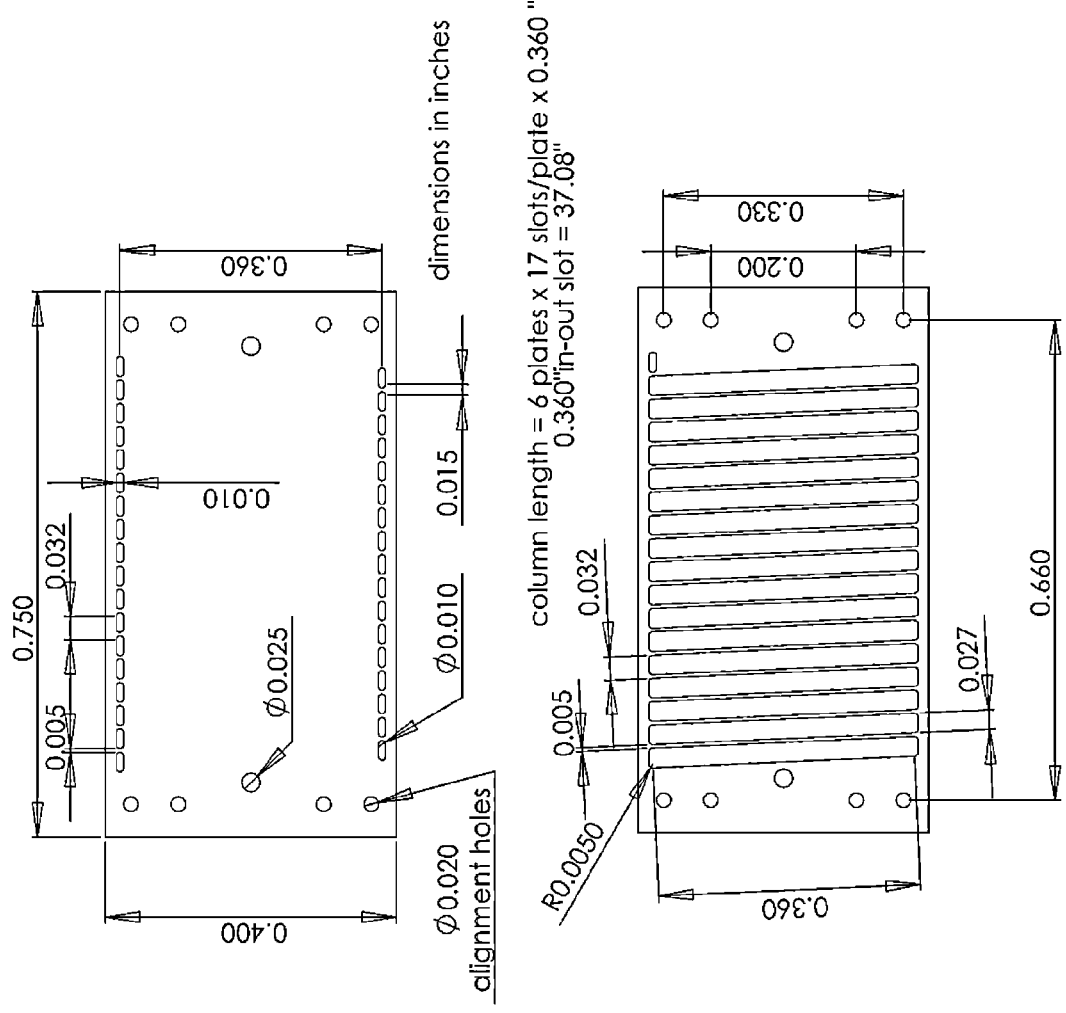
FIG. 7 is a schematic illustration of an example embodiment of the present invention.

FIG. 6 and FIG. 7 comprise a schematic illustration of an example embodiment of the present invention. Plate design and dimensions as shown in FIG. 6 and FIG. 7 can yield a column about 1 meter in length, with a cross section of about 0.005" by 0.027" (127 microns by 686 microns), with each pass about 0.340" (8636 microns) long. Each slot plate provides 17 channels for a total passage length of 5.78" (147 mm) per plate; for the 6 channel plates shown, the total passage length will be about 35". Adding additional lettered coupons, a-h, between the numbered coupons 5 and 6 will lengthen the column. Each duplicate lettered section will add about 5.80 (17×0.340) inches to the column length.

The resulting passages can be generally rectangular and provide a wide dimension to insure adequate flow through the column, while the short dimension enhances interaction with the sidewall of the column to improve chemical separations. In contrast to the circular cross section columns in U.S. Pat. No. 7,273,517, there are significantly fewer turn-around loops at the end of the channels so the flow disturbances that result from reversing the flow are reduced relative to the design in U.S. Pat. No. 7,273,517. Having a straight passage with a substantially uniform cross-section permits individual constituents in the flow to establish an equilibrium balance with the stationary phase on the column sidewalls. This enhances the ability of a column to separate the species, whereas turns and irregular cross-sections will enhance mixing in the flow and be detrimental to constituent separation. For the column dimensions shown in FIG. 6 and FIG. 7 the ratio of straight flow through a constant cross-section to a turning flow is on the order of 360:1. For a column constructed using the techniques presented in U.S. Pat. No. 7,273,517, the straight flow path to turn is on the order of 4:1.

In many gas chromatography applications, it can be important that the surfaces that contact the sample be cleaned and passivated to avoid the presence of active sites that may hold onto constituents of an analysis sample. Restek in Bellefonte, Pa. offers several commercial passivation treatments (U.S. Pat. Nos. 6,511,760 and 6,444,326, each of which is incorporated herein by reference) that can be suitable for use with the present invention. Other commercial passivation treatments can also be suitable. A thin coating (i.e., a stationary phase) can be deposited on the inner surface of the column to accomplish sample separation. Commonly, stationary phases are high molecular weight, thermally stable polymers in the form of liquids or gums. The most common are polysiloxanes and polyethylene glycols. Porous particles composed of polymers and zeolites are also common stationary phases. Several options for commercial GC column coatings are discussed in Chromatography Products, 2006 ed. by Restek Corp. (Lit. Cat. #580021), incorporated herein by reference.

Figure 8:
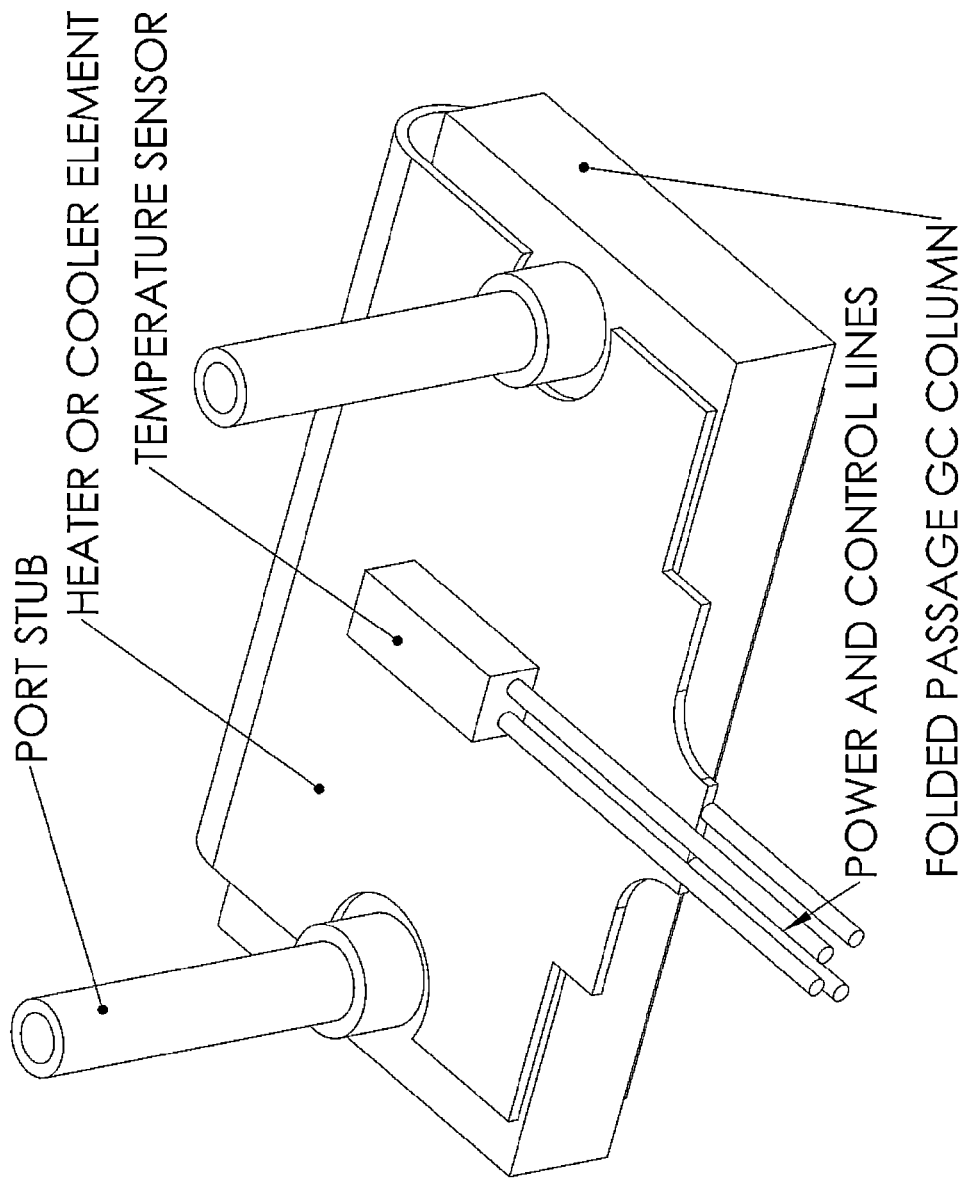
FIG. 8 is a schematic illustration of an example embodiment of the present invention.

Heaters and coolers can also be used with folded passage gas chromatography columns to enhance separations. High vapor pressure compounds can travel too fast through a gas chromatography column for adequate separation of individual constituents. By cooling the gas chromatography column, more volatile compounds will move more slowly through a column and sample separations will improve. Similarly, ramping the temperature of a miniature-gas chromatography column can help move low vapor pressure compounds in a timely manner at the top temperature of the ramp cycle, while maintaining the separation of high vapor pressure compounds at the lower temperatures of the ramp cycle. One configuration for this feature is illustrated in FIG. 8. The low mass of the folded passage gas chromatography enables the temperature to be controlled with a minimal input of power.

Figure 9:
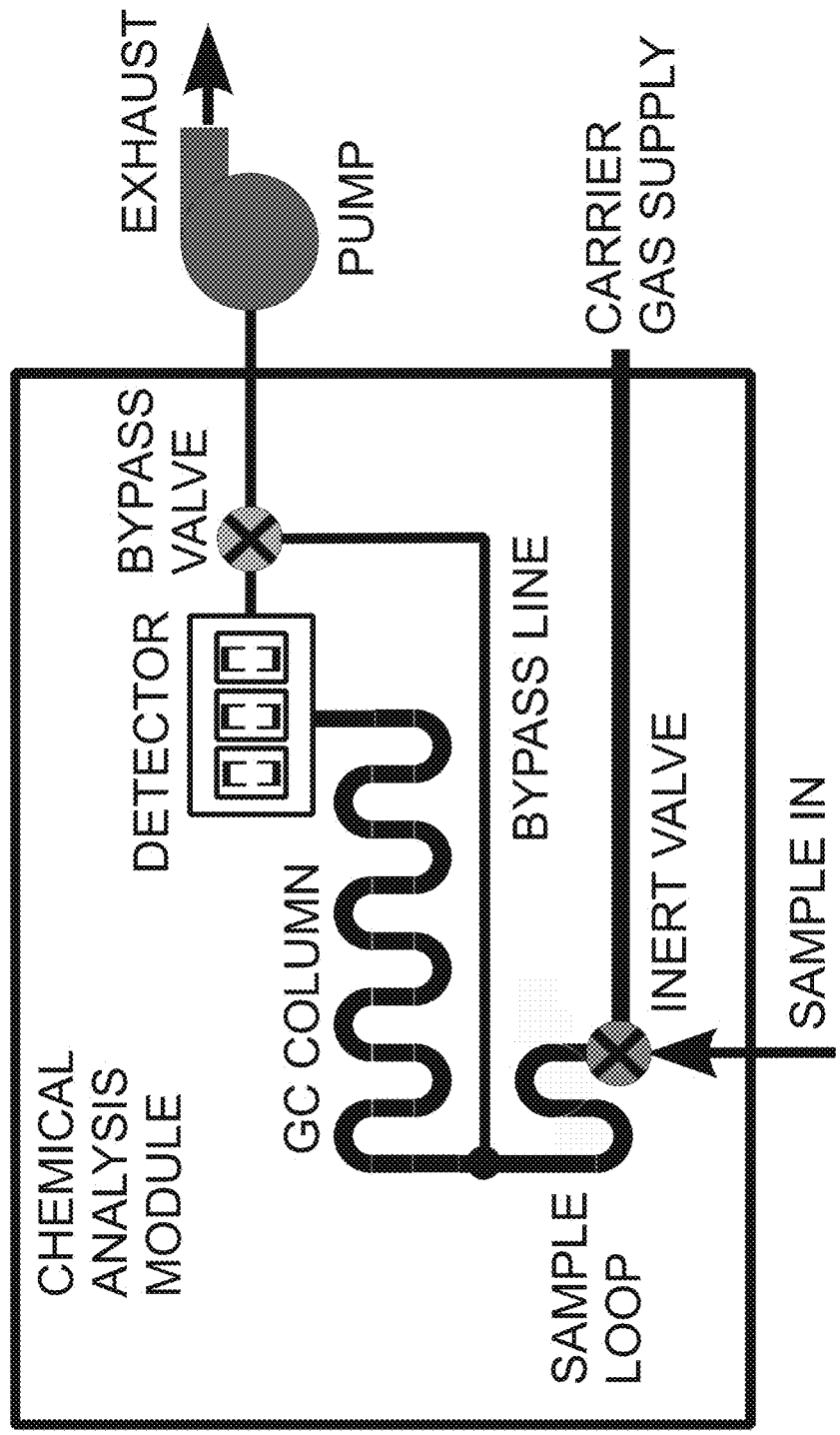
FIG. 9 is a schematic illustration of an example embodiment of the present invention.
Figure 10:
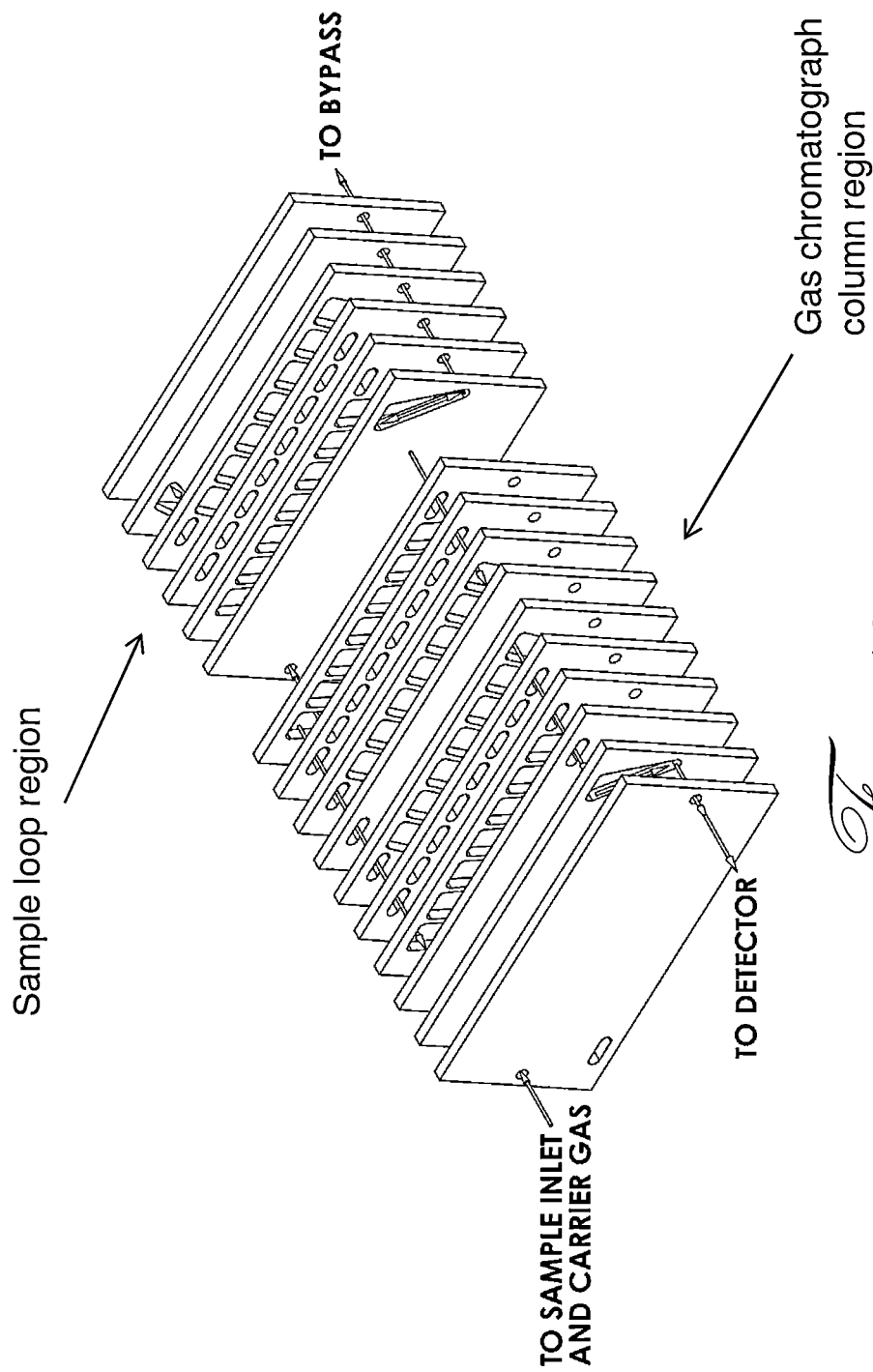
FIG. 10 is a schematic illustration of an example embodiment of the present invention.

A folded passage gas chromatography column according to the present invention can allow a sample loop to be integrated into the column. Sample loops are often used to introduce permanent gas samples into a gas chromatography column for analysis. Illustrated in FIG. 9 is a schematic of a sample-loop in a detector system. A gas sample is first pulled into the sample loop with a vacuum on the bypass line. The bypass valve then switches to apply vacuum on the gas chromatograph column, and the inert valve is switched to draw make-up gas from a clean carrier gas supply. The gas sample trapped in the sample loop is pulled through the gas chromatography column for analysis. FIG. 10 illustrates how a sample loop can be integrated into to a folded-passage gas chromatography column with minimum modifications from those described in connection with previous figures.

Figure 11:
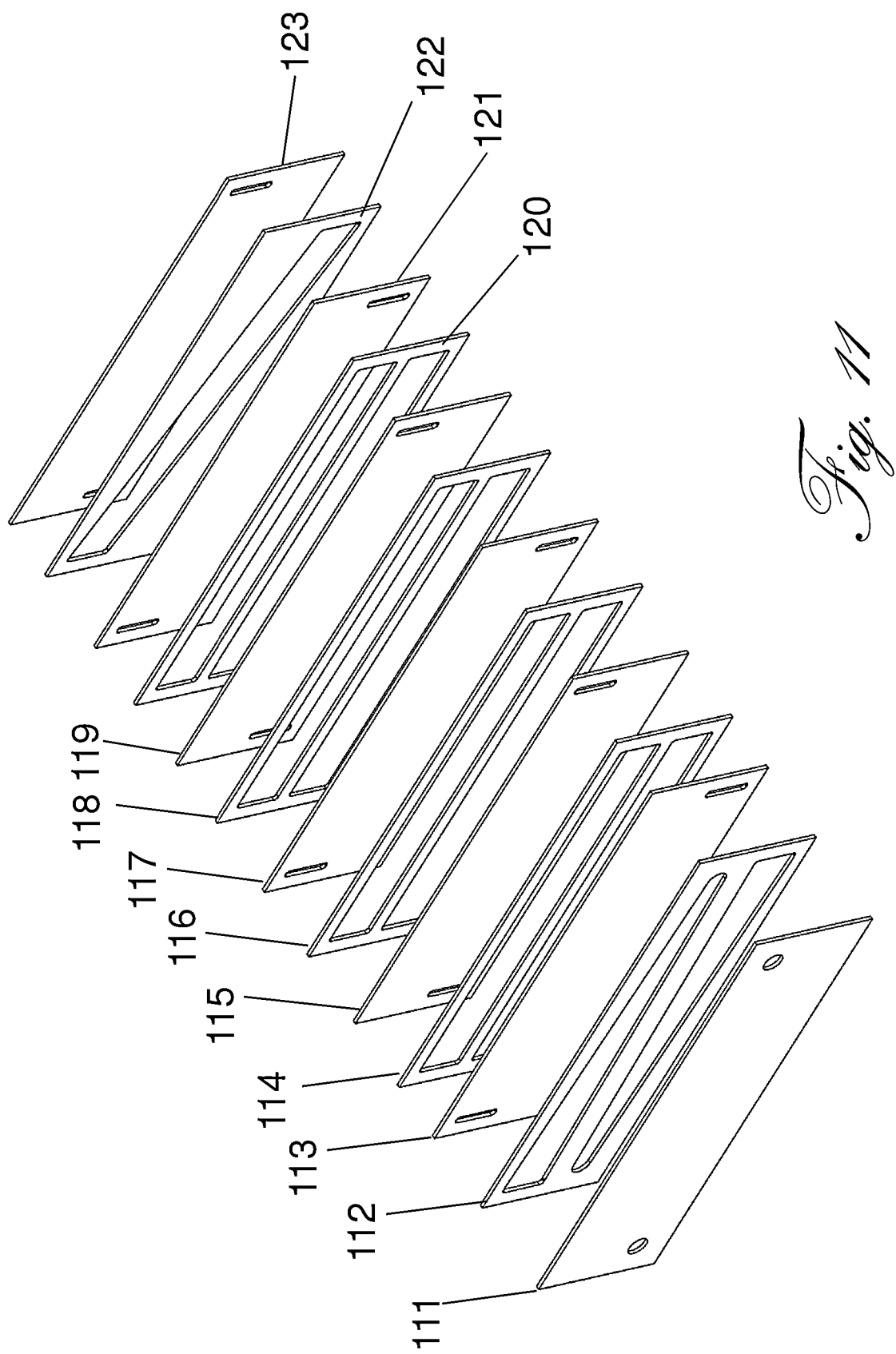
FIG. 11 is a schematic illustration of an example embodiment of the present invention.

Similarly, parallel sample loops can be integrated at the inlet of a folded-passage gas chromatography column to perform split flow analysis. In a split flow configuration, gas initially enters the folded-passage gas chromatography column from the sample loop but, at a predefined time, gas from a secondary parallel loop is introduced to truncate the sample loop flow and produce a sharper sample injection to the folded-passage gas chromatography column. Likewise, a folded-passage gas chromatography column can be upstream and in series with one or more other columns (folded-passage or conventional columns) to perform serial analyses on a sample FIG. 11 is a schematic illustration of an example embodiment of the present invention. In the example embodiment, a folded channel column transits each of several plates, then turns and transits the plates again. An entrance to the column comprises a port in plate 111, for example the opening at the left of the plate in the figure. The column then extends from left to right at the bottom of plate 112, then through the opening at the right of plate 113, and so on through plates 114-121. After transiting the opening at the right of plate 121, the column extends upward from right to left in the channel in plate 122, then through the opening at the left of plate 121 and then back through the top channels in plates 112-120, exiting through the opening at the right of plate 111.

Folded passage columns according to the present invention can provide several advantages over the prior art. They can be made with substantially uniform cross-sections, providing for low flow perturbation and thus enhanced gas separation. The design provides efficient channel packaging, allowing long columns in a small volume and with small packaging mass, which allows rapid heating and cooling with minimal power requirement. They can be made with wide, shallow channels, which can enhance gas interaction with the channel wall. They can be made in packages that are more rugged than traditional glass capillary and silicon gas chromatograph columns. The design facilitates implementation of a variety of column lengths by simple repetition or scaling of standard parts. The design is less sensitive to slight misalignments in fabrication as compared with other stack approaches, since misalignment will only manifest at the junctions between channels and slots; the relatively long channels in each plate are not affected by misalignment between plates.

The example embodiments described above contemplate pairs of channel plates for easy scalability; the invention includes other configurations of channels, such as combinations and subsets of the configurations described in connection with the example embodiments; e.g., a column can transit one or several channels in a first plate or subset of plates, then to one or more other plates or subset of plates, then later return through another channel or channels in the first plate or subset of plates. Those skilled in the art will appreciate other configurations of channels and slots that yield similar columns.

Folded passage columns according to the present invention can be constructed in various ways. As examples, the plates (also called "coupons") can be etched in metal using lithographic techniques known in the art. Coupons can also be stamped or laser cut in metal or ceramics. Coupons can also be cut with ultrasonic machining or waterjet cutting in compatible plate materials. Coupons can also be made with deposition techniques such as LIGA.

Coupons can be mounted with each other by techniques such as diffusion bonding, brazing, and clamping. Stubs for connection to external systems can be attached to the folded passage column by laser welding, soldering, brazing, resistive welding, spin welding, or other techniques compatible with the plate material. For plates of Pyrex-silicon, anodic bonding can also be suitable. The example embodiments described above contemplate rigid planar plates, but the invention can be suitable with curved plates or flexible plates, with appropriate matching curvature and plate bonding techniques.

The wall surfaces of a folded passage column can be coated using stationary phase deposition with solvent evaporation. They can be coated using dynamic coating, such as by passing a plug containing a solution of stationary phase through the length of the column. They can be coated by vapor phase deposition or chemical vapor deposition. The coating can be subsequently passivated to reduce interactions with the analytes and enhance adhesion of the stationary phase. They can be coated using chemical precipitation. They can be coated by packing with sorptive beads. They can be coated by introduction of pyrolyzing materials into the column.

Folded passage columns can be used in gas chromatographs in chemical detection systems. Folded passage columns can be configured to use as a heat exchanger, e.g., by configuring the channels and slots such that two substantially parallel columns are formed. Folded passage columns can be used with a thermal desorption preconcentrator or a flash vaporization injector. Folded passage columns can be used with detectors such as a microbalance, a thermal conductivity detector, a chemical impedance detector, or an ionization-based detector. Folded passage columns can be used as a solid phase extraction channel.

The particular sizes and equipment discussed above are cited merely to illustrate particular embodiments of the invention. It is contemplated that the use of the invention can involve components having different sizes and characteristics. It is intended that the scope of the invention be defined by the claims appended hereto.

We claim:

1. A fluid passage apparatus, having first and second ports for communication of fluid with a channel, comprising one or more elements defining a first surface and a second surface, wherein:
   a) the first surface has a first plurality of channels disposed therein, wherein each channel begins at a first end and extends to a second end, and wherein the channels do not intersect and do not reverse direction;
   b) the second surface has a second plurality of channels disposed therein, wherein each channel begins at a first end and extends to a second end, and wherein the channels do not intersect and do not reverse direction;
   c) wherein the ends of the channels in the first plurality of channels are in fluid communication with the ends of the channels in the second plurality of channels such that together the channels form a single continuous passage.

2. A fluid passage apparatus as in claim 1, wherein
   a) the second end of the ith channel in the first plurality of channels is in fluid communication with the first end of the ith channel in the second plurality of channels, for values of i from 1 to (n−1), where n is the number of channels in the first plurality of channels and the number of channels in the second plurality of channels;
   b) the second end of the ith channel in the second plurality of channels is in fluid communication with the first end of the (i+1)th channel in the first plurality of channels, for values of i from 1 to (n−1);

c) the first end of the first channel in the first plurality of channels is in fluid communication with the first port;

d) the second end of the nth channel in the second plurality of channels is in fluid communication with the second port.

3. A fluid passage apparatus as in claim 1, comprising:

a) a channel plate having first and second parallel surfaces, defining a plurality of channels extending into the plate from the first surface, and defining a plurality of channels extending into the plate from the second surface, and defining a plurality of slots connecting the ends of first surface channels with ends of second surface channels into a single continuous path;

b) a first cap plate mounted with the first surface of the channel plate such that the first cap plate and the channels form a passageway closed on three sides by the channel plate and on one side by the first cap plate, wherein the first cap plate defines a first opening in communication with the single path;

c) a second cap plate mounted with the second surface of the channel plate such that the second cap plate and the channels form a passageway closed on three sides by the channel plate and on one side by the second cap plate;

d) wherein at least one of the first cap plate and the second cap plate define a second opening therethrough in communication with the single path at the opposite end from the communication of the first opening.

4. A fluid passage apparatus as in claim 3, wherein the channel plate comprises metal, ceramic, or plastic.

5. A fluid passage apparatus as in claim 3, wherein the slots and channels have substantially the same cross-sectional area.

6. A fluid passage apparatus as in claim 1, comprising:

a) a first channel plate having first and second parallel surfaces, defining a plurality of channels extending into the plate from the first surface, and defining a plurality of slots placing the ends of first surface channels in communication with the second surface;

b) a second channel plate having a first surface, wherein the second channel plate is mounted with the first channel plate such that the second surface of the first channel plate sealingly engages the first surface of the second channel plate, and wherein the second channel plate defines a plurality of channels extending into the second channel plate from the first surface, wherein the plurality of channels are in communication with the slots such that the plurality of channels, combined with the plurality of slots and the plurality of channels in the first channel plate, form a single continuous path;

c) a first cap plate mounted with the first surface of the first channel plate such that the first cap plate and the channels form a passageway closed on three sides by the channel plate and on one side by the first cap plate;

d) wherein at least one of the first cap plate and the second channel plate define a first opening therethrough in communication with the single path;

e) wherein at least one of the first cap plate and the second channel plate define a second opening therethrough in communication with the single path at the opposite end from the communication of the first opening.

7. A fluid passage apparatus as in claim 1, comprising:

a) a first channel plate having first and second parallel surfaces, defining a plurality of channels extending into the first channel plate from the first surface, and defining a plurality of slots placing the ends of first surface channels in communication with the second surface;

b) a second channel plate having first and second parallel surfaces, defining a plurality of channels extending into the second channel plate from the first surface, and defining a plurality of slots placing the ends of first surface channels in communication with the second surface, wherein the second channel plate is mounted with the first channel plate such that the second surface of the first channel plate sealingly engages the second surface of the second channel plate, such that slots in the first channel plate are in communication with the slots in the second channel plate, and wherein the channels are disposed on the first and second channel plates such that the channels and the slots combine to form one continuous path;

c) a first cap plate mounted with the first surface of the first channel plate such that the first cap plate and the channels form a passageway closed on three sides by the first channel plate and on one side by the first cap plate, wherein the first cap plate defines a first opening in communication with the single path;

d) a second cap plate mounted with the first surface of the second channel plate such that the second cap plate and the channels form a passageway closed on three sides by the second channel plate and on one side by the second cap plate;

e) wherein at least one of the first cap plate and the second cap plate define a second opening therethrough in communication with the single path at the opposite end from the communication of the first opening.

8. A fluid passage apparatus as in claim 1, comprising:

a) a first channel plate having first and second surfaces, defining a plurality of channel openings extending through the first channel plate;

b) a second channel plate having first and second surfaces, defining a plurality of channel openings extending through the second channel plate;

c) a slot plate having first and second surfaces, and defining a plurality of slots extending through the slot plate;

d) wherein the first channel plate mounts with the slot plate such that the first surface of the first channel plate sealingly engages the first surface of the slot plate, and the second channel plate mounts with the slot plate such that the first surface of the second channel plate sealingly engages the second surface of the slot plate;

e) wherein the slots in the slot plate are disposed therein such that they are in communication with a channel in the first channel plate and with a channel in the second channel plate;

f) wherein the channels in the first channel plate and the channels in the second channel plate are disposed in their respective plates such that, when placed in communication through the slots in the slot plates, the channels form a single continuous path;

g) a first cap plate mounted with the second surface of the first channel plate such that the first cap plate and the channels in the first channel plate form a passageway closed on three sides by the first channel plate and on one side by the first cap plate, wherein the first cap plate defines a first opening in communication with the single path;

h) a second cap plate mounted with the second surface of the second channel plate such that the second cap plate and the channels in the second channel plate form a passageway closed on three sides by the second channel plate and on one side by the second cap plate;

i) wherein at least one of the first cap plate and the second cap plate define a second opening therethrough in communication with the single path at the opposite end from the communication of the first opening.

9. A gas chromatograph comprising a fluid passage apparatus as in claim 1, a sample input port in communication with a first port of the fluid passage apparatus, and a sample detector in communication with a second port of the fluid passage apparatus.

10. A gas chromatograph as in claim 9, further comprising a thermal control device mounted with the fluid passage apparatus.

11. A fluid passage apparatus as in claim 1, further comprising a heating element in thermal communication with the channel.

12. A fluid passage apparatus as in claim 11, wherein the heating element comprises a resistive heater in polyimide adhered to the apparatus.

13. A fluid passage apparatus as in claim 1, further comprising a cooling element in thermal communication with the channel.

14. A fluid passage apparatus as in claim 13, wherein the cooling element comprises a thermoelectric cooler such as a peltier cooler.

15. A fluid passage apparatus as in claim 1, further comprising a temperature sensor in thermal communication with the channel.

16. A fluid passage apparatus as in claim 1, wherein the single continuous passage has a substantially constant cross-sectional area.

17. A fluid passage apparatus as in claim 1, wherein the channels define a fluid passageway having a cross-section in the shape of a trapezoid.

18. A fluid passage apparatus as in claim 1, wherein the channels define a fluid passageway having a cross-section in the shape of a parallelogram.

19. A fluid passage apparatus as in claim 1, wherein the elements comprise a module that is repeated multiple times to form the single continuous passageway.

20. A fluid passage apparatus as in claim 1, wherein the elements comprise one or more substantially planar elements.

21. A fluid passage apparatus as in claim 1, wherein the length of a first channel in a first surface is at least 10 times greater than the length of fluid communication between said first channel and a channel in a second surface.

22. A fluid passage apparatus comprising a body having a folded passage column therein, wherein the body comprises a plurality of surfaces, each having one or more channels, that do not reverse direction, formed therein; and wherein at least one channel in a first surface is in communication with at least one channel in a second surface, comprising a plurality of modules, each module in fluid communication with either another module or with a port, wherein each module comprises:
   a) a first channel plate having first and second surfaces, defining a plurality of channel openings extending through the first channel plate;
   b) a second channel plate having first and second surfaces, defining a plurality of channel openings extending through the second channel plate;
   c) a slot plate having first and second surfaces, and defining a plurality of slots extending through the slot plate;
   d) wherein the first channel plate mounts with the slot plate such that the first surface of the first channel plate sealingly engages the first surface of the slot plate, and the second channel plate mounts with the slot plate such that the first surface of the second channel plate sealingly engages the second surface of the slot plate;
   e) wherein the slots in the slot plate are disposed therein such that they are in communication with a channel in the first channel plate and with a channel in the second channel plate;
   f) wherein the channels in the first channel plate and the channels in the second channel plate are disposed in their respective plates such that, when placed in communication through the slots in the slot plates, the channels form a single continuous path.

23. A method of making a fluid passage apparatus, comprising:
   a) forming in a first channel plate a plurality of channel openings therethrough;
   b) forming in a second channel plate a plurality of channel openings therethrough;
   c) forming in a slot plate a plurality of slot openings therethrough;
   d) mounting the slot plate between the first and second channel plates such that the slot plate sealingly engages the first channel plate and the second channel plate;
   e) mounting a first end cap with the first channel plate such that the first end cap sealingly engages the first channel plate;
   f) mounting a second end cap with the second channel plate such that the second end cap sealingly engages the second channel plate;
   g) wherein the channels and slots are disposed such that they combine to form a single continuous path.

24. A method as in claim 23, wherein the first channel plate is metal, ceramic, or plastic, and wherein forming channel openings in the first channel plate comprises machining the first channel plate.

25. A method as in claim 23, wherein the first channel plate is metal, ceramic, or plastic, and wherein forming channel openings in the first channel plate comprises stamping, etching or laser cutting the first channel plate.

26. A method as in claim 23, wherein the first channel plate is formed by a deposition technique.

27. A method as in claim 23, wherein mounting the slot plate between the first and second channel plates comprises diffusion bonding or brazing.

28. A method as in claim 23, wherein the first and second channel plates comprise glass, the slot plate comprises glass, and wherein mounting the slot plate between the first and second channel plates comprises anodic bonding.

29. A method as in claim 23, further comprising coating the interior surfaces of the single path.

30. A method as in claim 29, wherein coating the interior surfaces comprises one or more of stationary phase deposition with solvent evaporation, dynamic coating, vapor deposition, chemical precipitation, packing with sorptive beads, porous monolith, or introducing pyrolizing materials into the single path.

* * * * *